(12) United States Patent
Ahrens et al.

(10) Patent No.: US 10,167,481 B2
(45) Date of Patent: *Jan. 1, 2019

(54) PLANT REGULATORY ELEMENTS AND USES THEREOF

(71) Applicant: Monsanto Technology LLC, St. Louis, MO (US)

(72) Inventors: Jeffrey E. Ahrens, Manchester, MO (US); Shoba Cherian, Bangalore (IN); Paul J. Loida, St. Louis, MO (US); Linda L. Lutfiyya, St. Louis, MO (US); Wei Wu, St. Louis, MO (US); Jiali Xie, Ballwin, MO (US)

(73) Assignee: Monsanto Technology LLC, St. Louis, MO (US)

(*) Notice: Subject to any disclaimer, the term of this patent is extended or adjusted under 35 U.S.C. 154(b) by 106 days.

This patent is subject to a terminal disclaimer.

(21) Appl. No.: 15/179,607

(22) Filed: Jun. 10, 2016

(65) Prior Publication Data

US 2016/0298127 A1 Oct. 13, 2016

Related U.S. Application Data

(62) Division of application No. 13/830,403, filed on Mar. 14, 2013, now Pat. No. 9,663,793.

(60) Provisional application No. 61/635,945, filed on Apr. 20, 2012.

(51) Int. Cl.
*C12N 15/82* (2006.01)
*C12N 15/113* (2010.01)

(52) U.S. Cl.
CPC ........ *C12N 15/8234* (2013.01); *C12N 15/113* (2013.01); *C12N 15/8216* (2013.01); *C12N 15/8222* (2013.01); *C12N 15/8237* (2013.01)

(58) Field of Classification Search
None
See application file for complete search history.

(56) References Cited

U.S. PATENT DOCUMENTS

| 7,642,347 B2 * | 1/2010 | Dasgupta | C12N 15/8223 |
| | | | 435/320.1 |
| 9,663,793 B2 * | 5/2017 | Ahrens | C12N 15/8216 |
| 2002/0192813 A1 | 12/2002 | Conner et al. | |

(Continued)

FOREIGN PATENT DOCUMENTS

| CN | 101939436 A | 1/2011 |
| EP | 0459643 A2 | 12/1991 |

(Continued)

OTHER PUBLICATIONS

Rombauts et al. PlantCARE, a plant cis-acting regulatory element database. Nucleic Acids Research. 1999. 27(1): 295-296.*

(Continued)

*Primary Examiner* — Ashley K Buran
(74) *Attorney, Agent, or Firm* — Dentons US LLP; Carine M. Doyle, Esq.

(57) ABSTRACT

The present invention provides DNA molecules and constructs, and their nucleotide sequences, useful for modulating gene expression in plants. Transgenic plants, plant cells, plant parts, and seeds comprising the DNA molecules operably linked to heterologous transcribable polynucleotides are also provided, as are methods of their use.

14 Claims, 2 Drawing Sheets

Specification includes a Sequence Listing.

(56) References Cited

U.S. PATENT DOCUMENTS

| | | | |
|---|---|---|---|
| 2006/0272045 A1* | 11/2006 | Hinkle | C12N 15/8225 800/278 |
| 2008/0263721 A9 | 10/2008 | Boukharov et al. | |
| 2009/0106857 A1* | 4/2009 | Niu | C07K 14/415 800/278 |
| 2011/0177228 A1 | 7/2011 | Alexandrov et al. | |

FOREIGN PATENT DOCUMENTS

| | | |
|---|---|---|
| JP | A-H7-067645 | 3/1995 |
| JP | A-2010-500035 | 1/2010 |
| RU | 2237717 C2 | 10/2004 |
| WO | WO 2005/113771 | 12/2005 |
| WO | WO 2008/021974 A1 | 2/2008 |
| WO | WO 2009/052476 | 4/2009 |
| WO | WO 2010/117737 A1 | 10/2010 |
| WO | WO 2011/088299 A1 | 7/2011 |
| WO | WO 2013/158227 | 10/2013 |

OTHER PUBLICATIONS

Ross et al. Activation of the *Oryza sativa* non-symbiotic haemoglobin-2 promoter by the cytokinin-regulated transcription factor, ARR1. Journal of Experimental Biology. 2004. 55(403): 1721-1731.*

Kim et al. A 20 nucleotide upstream element is essential for the nopaline synthase (nos) promoter activity. Plant Molecular Biology. 1994. 24: 105-117.*

Fang et al. Systematic sequence analysis and identification of tissue-specific or stress-responsive genes of NAC transcription factor family in rice. Mol. Genet. Genomics. 2008. 280: 547-563.*

USPTO: Final Office Action regarding U.S. Appl. No. 13/830,403, dated Sep. 30, 2016.

Response to Final Office Action regarding U.S. Appl. No. 13/830,403, dated Dec. 15, 2016.

USPTO: Supplemental Notice of Allowance and Fees Due regarding U.S. Appl. No. 13/830,403, dated Feb. 28, 2017.

Office Action regarding Russian Application No. 2014146581-10, dated Apr. 4, 2017.

Donald et al., "Mutation of either G box or I box sequences profoundly affects expression from the *Arabidopsis* rbcS-1A promoter," The EMBO Journal 9(6):1717-1726, 1990.

Office Action regarding Chinese Application No. 2013800317960, dated Jul. 26, 2016.

Wang, "Structure and Classification of Promoters," *Advance in Life Science Research* pp. 2-8, 2008.

USPTO: Notice of Allowability regarding U.S. Appl. No. 13/830,403, dated Apr. 25, 2017.

Office Action regarding Russian Application No. 2014146581-10, dated Dec. 14, 2016.

GenBank Accession No. EU956242.1, dated Dec. 10, 2008.

Office Action regarding Japanese Application No. 2015-507054, dated Jan. 10, 2017.

Bioinformatics: Sequence and Genome Analysis (Japanese version), 2005, second version, pp. 350-355 and 362-368.

Japanese Journal of Soil Science and Plant Nutrition, 2006, vol. 77, No. 2, pp. 213-218.

USPTO: Notice of Allowance and Fees Due regarding U.S. Appl. No. 13/830,403, dated Jan. 17, 2017.

Benfey et al., "The CaMV 35S enhancer contains at least two domains which can confer different developmental and tissue-specific expression patterns," *EMBO J* 8(8):2195-2202, 1989.

Cho et al., "Regulation of root hair initiation and expansin gene expression in *Arabidopsis*," *Plant Cell* 14:3237-3253, 2002.

Kim et al., "A 20 nucleotide upstream element is essential for the nopaline synthase (nos) promoter activity," *Plant Mol Biol* 24(1):105-117, 1994.

Odell et al., "Identification of DNA sequences required for activity of the cauliflower mosaic virus 35S promoter," *Nature* 313:810-812, 1985.

Piechulla et al., "Identification of tomato Lhc promoter regions necessary for circadian expression," *Plant Molec Biol* 38(4):655-662, 1998.

Welsch et al., "Structural and functional characterization of the phytoene synthase promoter from *Arabidopsis thaliana*," *Planta* 216:523-534, 2003.

Supplementary European Search Report regarding Application No. EP 13777634, dated Oct. 9, 2015.

EMBL Accession No. AC191666, dated Sep. 25, 2006.

Liu et al., "Cloning and characterization of a transcription factor ZmNAC1 in maize (*Zea mays*)," found at <<http://pub.chinasciencejournal.com/Hereditas(Beijing)/31418.jhtml>>, accessed on Sep. 25, 2015.

Puranik et al., "NAC proteins: regulation and role in stress tolerance," *Trends in Plant Science* 17(6):369-381, 2012.

Nogueira et al., "SsNAC23, a member of the NAC domain protein family, is associated with cold, herbivory and water stress in sugarcane," *Plant Science* 169:93-106, 2005.

GenBank Accession No. AY742218, dated Jun. 14, 2005.

GenBank Accession No. AAW62955, dated Jun. 14, 2005.

Clontech, "GenomeWalker Universal Kit User Manual," Clontech Laboratories, pp. 1-30, 2007.

GenBank Accession No. ACG28360.1, dated Dec. 10, 2008.

Nakashima et al., "Functional analysis of a NAC-type transcription factor OsNAC6 involved in abiotic and biotic stress-responsive gene expression in rice," *The Plant Journal* 51:617-630, 2007.

Di Pierro et al., "A point mutation affecting an SP1 binding site in the promoter of the ferrochelatase gene impairs gene transcription and causes erythropoietic protoporphyria," *Experimental Hematology* 33:584-591, 2005.

* cited by examiner

US 10,167,481 B2

PLANT REGULATORY ELEMENTS AND USES THEREOF

REFERENCE TO RELATED APPLICATIONS

This application is a divisional of U.S. application Ser. No. 13/830,403, filed Mar. 14, 2013, which application claims the benefit of U.S. provisional application No. 61/635,945, filed Apr. 20, 2012, the disclosure of each of which is herein incorporated by reference in its entirety.

INCORPORATION OF SEQUENCE LISTING

The sequence listing that is contained in the file named "MONS326US_ST25.txt," which is 22,497 bytes (as measured in Microsoft Windows®) and was created on Mar. 14, 2013, is filed herewith by electronic submission and is incorporated by reference herein.

FIELD OF THE INVENTION

The present invention relates to the field of plant molecular biology and plant genetic engineering. More specifically, the present invention relates to DNA molecules useful for modulating gene expression in plants.

BACKGROUND OF THE INVENTION

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

Transgenic crops expressing transgenes that confer an advantage to a plant during germination in cold and wet stress conditions require regulatory elements that possess patterns of expression in tissues that are most beneficial for the expression of such transgenes. Such regulatory elements should be expressed sufficiently in the developing seed as to enable the storage of transgene products that can act quickly when the seed germinates under cold and/or wet conditions, as well as provide expression during the early stages of germination and seedling establishment. Accordingly, the present invention provides novel regulatory elements that demonstrate higher levels of expression in the developing and germinating seed and can be used to drive expression of transgenes that provide benefit under cold and/or wet germination conditions.

SUMMARY OF THE INVENTION

The present invention provides novel gene regulatory elements for use in plants. The present invention also provides DNA constructs comprising the regulatory elements. The present invention also provides transgenic plant cells, plants, and seeds comprising the regulatory elements. The sequences may be provided operably linked to a transcribable polynucleotide molecule. In one embodiment, the transcribable polynucleotide molecule may be heterologous with respect to a regulatory sequence provided herein. A regulatory element sequence provided by the invention thus may, in particular embodiments, be defined as operably linked to a heterologous transcribable polynucleotide molecule. The present invention also provides methods of making and using the regulatory elements, the DNA constructs comprising the regulatory elements, and the transgenic plant cells, plants, and seeds comprising the regulatory elements operably linked to a transcribable polynucleotide molecule.

In one aspect, the invention provides a DNA molecule comprising a DNA sequence selected from the group consisting of: (a) a sequence with at least about 85 percent sequence identity to any of SEQ ID NOs: 1, 2, 3, 4, 6, or 8; (b) a sequence comprising any of SEQ ID NOs: 1, 2, 3, 4, 6, or 8; and (c) a fragment of any of SEQ ID NOs: 1, 2, 3, 4, 6, or 8, wherein the fragment has gene regulatory activity, wherein said sequence is operably linked to a heterologous transcribable polynucleotide molecule. In one embodiment, the DNA molecule has at least about 90 percent sequence identity to the DNA sequence of any of SEQ ID NOs: 1, 2, 3, 4, 6, or 8. In another embodiment, the DNA molecule has at least 95 percent sequence identity to the DNA sequence of any of SEQ ID NOs: 1, 2, 3, 4, 6, or 8. In another embodiment, the DNA sequence comprises gene regulatory activity. In still another embodiment, the heterologous transcribable polynucleotide molecule comprises a gene of agronomic interest. In other embodiments, the gene of agronomic interest confers herbicide tolerance or pest resistance in plants.

In another aspect, the present invention provides a transgenic plant cell comprising a heterologous DNA molecule comprising a sequence selected from the group consisting of: (a) a sequence with at least about 85 percent sequence identity to any of SEQ ID NOs: 1, 2, 3, 4, 6, or 8; (b) a sequence comprising any of SEQ ID NOs: 1, 2, 3, 4, 6, or 8; and (c) a fragment of any of SEQ ID NOs: 1, 2, 3, 4, 6, or 8, wherein the fragment has gene-regulatory activity, wherein said sequence is operably linked to a heterologous transcribable polynucleotide molecule. In embodiments, the transgenic plant cell may be a monocotyledonous plant cell or a dicotyledonous plant cell.

In other embodiments, the invention provides a transgenic plant, or part thereof, comprising a DNA molecule selected from the group consisting of: (a) a sequence with at least about 85 percent sequence identity to any of SEQ ID NOs: 1, 2, 3, 4, 6, or 8; (b) a sequence comprising any of SEQ ID NOs: 1, 2, 3, 4, 6, or 8; and (c) a fragment of any of SEQ ID NOs: 1, 2, 3, 4, 6, or 8, wherein the fragment has gene regulatory activity, wherein said sequence is operably linked to a heterologous transcribable polynucleotide molecule. In another embodiment, the invention provides a progeny plant of any generation of such a transgenic plant, or a part thereof, wherein the progeny plant or part comprises the DNA molecule as described above. In still another embodiment, the invention provides a transgenic seed, wherein the seed comprises DNA molecule as described above.

In another aspect, the invention provides a transgene cassette comprising a transcriptional regulatory expression element group selected from the group consisting of SEQ ID NOs: 1, 6, and 8, wherein the transcriptional regulatory expression element group is operably linked to a heterologous coding sequence that is operably linked to a 3' UTR selected from the group consisting of SEQ ID NOs: 10, 11, 12, and 13. In an embodiment, the transgene cassette comprises the transcriptional regulatory expression element group presented as SEQ ID NO:1, wherein the transcriptional regulatory expression element group is operably linked to a heterologous coding sequence that is operably linked to the 3' UTR presented as SEQ ID NO:10. In another embodiment, the transgene cassette comprises the transcriptional regulatory expression element group presented as SEQ ID NO:6, wherein the transcriptional regulatory expression element group is operably linked to a heterologous coding sequence that is operably linked to a 3' UTR selected from the group consisting of SEQ ID NOs:11 and 12. In still another embodiment, the transgene cassette comprises the transcriptional regulatory expression element group presented as SEQ ID NO:8, wherein the transcriptional regulatory expression element group is operably linked to a heterologous coding sequence that is operably linked to a 3' UTR selected from the group consisting of SEQ ID NOs:12 and 13. In another embodiment, the invention provides a method of producing a commodity product comprising obtaining a transgenic plant or part thereof comprising a DNA sequence selected from the group consisting of: (a) a sequence with at least about 85 percent sequence identity to any of SEQ ID NOs: 1, 2, 3, 4, 6, or 8; (b) a sequence comprising any of SEQ ID NOs: 1, 2, 3, 4, 6, or 8; and (c) a fragment of any of SEQ ID NOs: 1, 2, 3, 4, 6, or 8, wherein the fragment has gene regulatory activity, wherein said sequence is operably linked to a heterologous transcribable polynucleotide molecule, and producing the commodity product therefrom. In an embodiment, the commodity product is protein concentrate, protein isolate, grain, starch, seeds, meal, flour, biomass, or seed oil.

In another aspect, the invention provides a method of expressing a transcribable polynucleotide molecule comprising obtaining a transgenic plant comprising a DNA sequence selected from the group consisting of: (a) a sequence with at least about 85 percent sequence identity to any of SEQ ID NOs: 1, 2, 3, 4, 6, or 8; (b) a sequence comprising any of SEQ ID NOs: 1, 2, 3, 4, 6, or 8; and (c) a fragment of any of SEQ ID NOs: 1, 2, 3, 4, 6, or 8, wherein the fragment has gene regulatory activity, wherein said sequence is operably linked to a heterologous transcribable polynucleotide molecule, and cultivating the plant, wherein the transcribable polynucleotide is expressed.

BRIEF DESCRIPTION OF THE SEQUENCES

Figure 1:
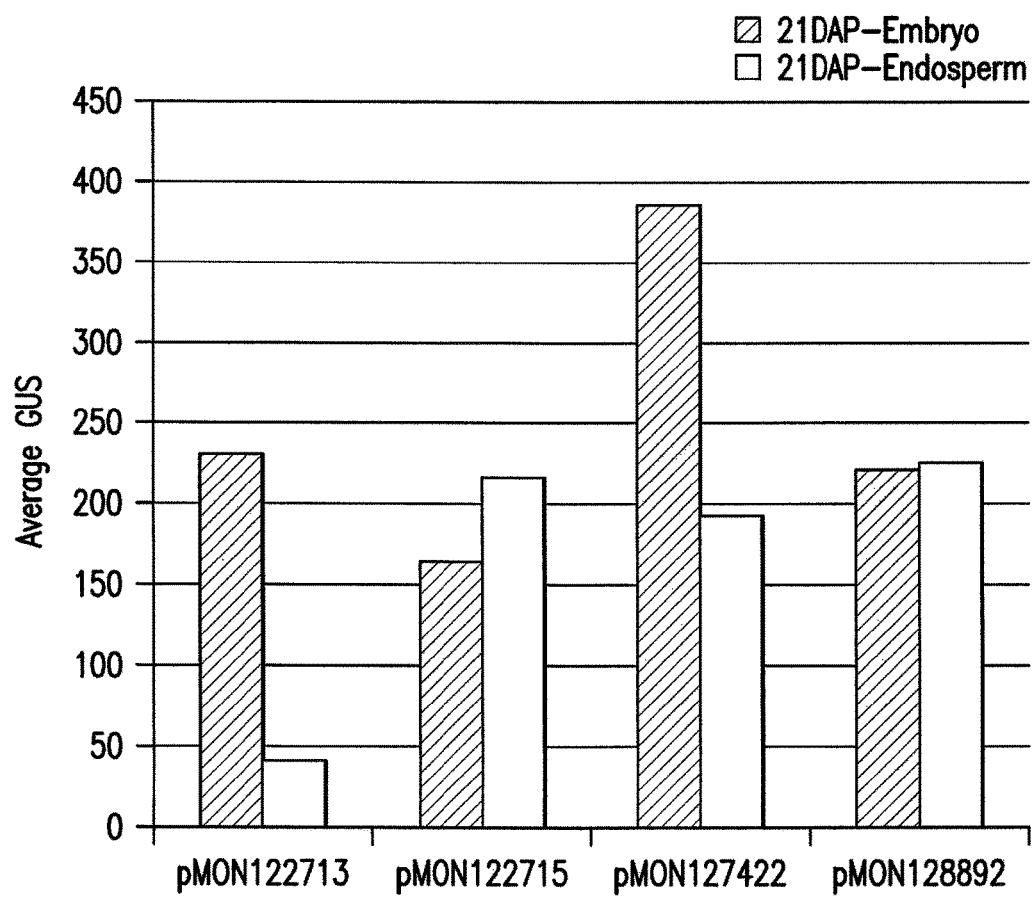
FIG. 1—shows β-glucuronidase (GUS) expression in transgenic developing corn embryo and endosperm tissues imparted by different transgene cassette configurations. Each transgene cassette configuration is comprised of the GUS coding sequence operably linked to the transcriptional regulatory expression element groups EXP-Zm.Nac+Os-.FBA:1:1 (SEQ ID NO:6) and EXP-Zm.Nac+Os.Cab-1:1:1 (SEQ ID NO:8) and the 3' UTRs T-Os.CLUS33428_1-1:1:1 (SEQ ID NO:11), T-Os.Mth-1:1:1 (SEQ ID NO:12), and T-Os.Ara5-1:1:1 (SEQ ID NO:13), as shown in Table 3 of Example 3.

SEQ ID NO:1—sequence of a transcriptional regulatory expression element group or EXP, EXP-Zm.Nac+Zm.DnaK: 1:1, comprised of the promoter, P-Zm.Nac-1:1:2 (SEQ ID NO:2), which is operably linked 5' to the leader, L-Zm.Nac-1:1:1 (SEQ ID NO:4), which is operably linked to the intron, I-Zm.DnaK-1:1:1 (SEQ ID NO:5).

SEQ ID NO:2—sequence of the promoter, P-Zm.Nac-1: 1:2.

SEQ ID NO:3—sequence comprised of the promoter, P-Zm.Nac-1:1:2 (SEQ ID NO:2), which is operably linked 5' to the leader, L-Zm.Nac-1:1:1 (SEQ ID NO:4).

SEQ ID NO:4—sequence of the leader, L-Zm.Nac-1:1:1.

SEQ ID NO:5—sequence of the intron, I-Zm.DnaK-1:1: 1.

SEQ ID NO:6—sequence of a transcriptional regulatory expression element group or EXP, EXP-Zm.Nac+Os.FBA: 1:1, which is comprised of the promoter, P-Zm.Nac-1:1:2 (SEQ ID NO:2), which is operably linked 5' to the leader, L-Zm.Nac-1:1:1 (SEQ ID NO:4), which is operably linked to the intron, I-Os.FBA-1-1:1:1 (SEQ ID NO:7).

SEQ ID NO:7—sequence of the intron, I-Os.FBA-1-1:1: 1.

SEQ ID NO:8—sequence of a transcriptional regulatory expression element group or EXP, EXP-Zm.Nac+Os.Cab-1:1:1, which is comprised of the promoter, P-Zm.Nac-1:1:2 (SEQ ID NO:2), which is operably linked 5' to the leader, L-Zm.Nac-1:1:1 (SEQ ID NO:4), which is operably linked to the intron, I-Os.Cab-1-1:1:1 (SEQ ID NO:9).

SEQ ID NO:9-sequence of the intron, I-Os.Cab-1-1:1:1.

SEQ ID NO:10-sequence of the 3' UTR, T-AGRtu.nos-1:1:13.

SEQ ID NO:11-sequence of the 3' UTR, T-Os-.CLUS33428_1-1:1:1.

SEQ ID NO:12-sequence of the 3' UTR, T-Os.Mth-1:1:1.

SEQ ID NO:13-sequence of the 3' UTR, T-Os.Ara5-1:1:1.

SEQ ID NO:14-coding sequence of the β-glucuronidase marker gene.

SEQ ID NO:15-sequence of a transcriptional regulatory expression element group or EXP, EXP-CaMV.35S:1:1, comprising the cauliflower mosaic virus (CaMV) 35S promoter and leader.

SEQ ID NO:16-sequence of a transcriptional regulatory expression element group or EXP, EXP-Os.Act1:1:1, comprising the rice actin 1 promoter, leader, and intron.

DETAILED DESCRIPTION OF THE INVENTION

The present invention provides novel polynucleotide molecules having beneficial gene regulatory activity from plant species. The invention also provides DNA constructs comprising the regulatory elements, as well as transgenic plant cells, plants, and seeds comprising the regulatory elements. The nucleotide sequences of these polynucleotide molecules are provided as SEQ ID NOs: 1, 2, 3, 4, 6, and 8. The design, construction, and use of these polynucleotide molecules are provided by the invention. These polynucleotide molecules are capable of, for example, affecting the expression of an operably linked transcribable polynucleotide molecule in plant tissues, and therefore selectively regulating gene expression or activity of an encoded gene product in transgenic plants. The present invention also provides methods of making and using the regulatory elements, the DNA constructs comprising the promoters and/or other disclosed nucleotide sequences, and methods for preparing and using the same. The invention also provides transgenic plant cells, plants, and seeds comprising the regulatory elements operably linked to a transcribable polynucleotide molecule, as well as transformed host cells.

DNA sequences according to the present invention may be provided operably linked to a transcribable polynucleotide molecule. In one embodiment, the transcribable polynucleotide molecule may be heterologous with respect to a regulatory sequence provided herein. A regulatory element sequence provided by the invention thus may, in particular embodiments, be defined as operably linked to a heterologous transcribable polynucleotide molecule.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, as disclosed in the present invention. For example, polymerase chain reaction (PCR) technology can be used to amplify a particular starting DNA molecule and/or to produce variants of the original molecule. DNA molecules, or fragment thereof, can also be obtained by other techniques, such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1, 2, 3, 4, 6, and 8.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, in one embodiment, the invention provides a DNA molecule comprising a sequence that, when optimally aligned to a reference sequence, provided herein as SEQ ID NOs: 1, 2, 3, 4, 6, and 8, has at least about 85 percent identity, at least about 90 percent identity, at least about 95 percent identity, at least about 96 percent identity, at least about 97 percent identity, at least about 98 percent identity, or at least about 99 percent identity to the reference sequence. In particular embodiments, such sequences may be defined as having gene-regulatory activity.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group (EXP) may be comprised of expression elements, such as enhancers, promoters, leaders, and introns, operably linked. Thus, a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and may be further comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders, that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects, such as by their temporal, spatial, developmental, tissue, environmental, physiological, pathological, cell cycle, and/or chemically responsive expression pattern, and any combination thereof, as well as by quantitative or qualitative indications. A promoter may be useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as an mRNA, a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, i.e. a promoter produced through the fusion of two or more heterologous DNA molecules. A promoter useful in practicing the present invention may include SEQ ID NO:3, or fragments or variants thereof. In specific embodiments of the invention, such molecules and any variants or derivatives thereof as described herein are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" that provides a basal level of transcription and is comprised of a TATA box or equivalent sequence for recognition and binding of the RNA polymerase II complex for initiation of transcription.

In one embodiment, the invention provides fragments of a promoter sequence as disclosed herein. Promoter fragments may comprise promoter activity as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from the promoter presented as SEQ ID NO:3, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Compositions derived from the promoter presented as SEQ ID NO:3, comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. The promoter presented as SEQ ID NO:3 and fragments or enhancers derived there from can be used to make chimeric transcriptional regulatory element compositions comprised the promoter presented as SEQ ID NO:3 and the fragments or enhancers derived there from operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. A leader useful in practicing the present invention presented as SEQ ID NO:4 or fragments or variants thereof. In specific embodiments, such sequences may be provided defined as being capable of acting as a leader in a host cell, including, for example, a transgenic plant cell. In one embodiment, such sequences are decoded as comprising leader activity.

The leader sequence (5' UTR) presented as SEQ ID NO:4 may be comprised of regulatory elements or may adopt secondary structures that can have an effect on transcription or translation of a transgene. This leader sequence may be used in accordance with the present invention to make chimeric regulatory elements that affect transcription or translation of a transgene. In addition, the leader sequence presented as SEQ ID NO:4 can be used to make chimeric leader sequences that affect transcription or translation of a transgene.

The introduction of a foreign gene into a new plant host does not always result in high expression of the incoming gene. Furthermore, if dealing with complex traits, it is sometimes necessary to modulate several genes with spatially or temporally different expression pattern. Introns can principally provide such modulation. However, multiple uses of the same intron in one plant has been shown to exhibit disadvantages. In those cases, it is necessary to have a collection of basic control elements for the construction of appropriate recombinant DNA elements. The number of introns known in the art to have expression-enhancing properties is limited, and thus, alternatives are needed.

Compositions derived from any of the introns presented as SEQ ID NOs:5, 7, and 9 can be comprised of internal deletions or duplications of cis regulatory elements. Additionally, alterations of the 5' and 3' sequences comprising the intron/exon splice junctions may be used to improve expression or specificity of expression when operably linked to a promoter+leader or chimeric promoter+leader and coding sequence. Alterations of the 5' and 3' regions comprising the intron/exon splice junction may also be made to reduce the potential for introduction of false start and stop codons produced in the resulting transcript after processing and splicing of the messenger RNA. The introns can be tested empirically as described in the working examples to determine the intron's effect on expression of a transgene.

In accordance with the present invention, a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of a promoter having a similar expression pattern to the original promoter.

As used herein, the term "enhancer" or "enhancer element" refers to a cis-acting transcriptional regulatory element (a cis-element), which confers an aspect of the overall expression pattern, but is usually insufficient alone to drive transcription of an operably linked polynucleotide sequence. Unlike promoters, enhancer elements do not usually include a transcription start site (TSS), or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that affect the transcription of operably linked genes. Many promoter enhancer elements are believed to bind DNA-binding proteins and/or affect DNA topology, producing local conformations that selectively allow or restrict access of RNA polymerase to the DNA template, or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes [e.g., tubA1, Adh1, Sh1, Ubi1 (Jeon et al., *Plant Physiol.* 123:1005-1014, 2000; Callis et al., *Genes Dev.* 1:1183-1200, 1987; Vasil et al., *Plant Physiol.* 91:1575-1579, 1989; Christiansen et al., *Plant Mol. Biol.* 18:675-689, 1992) and in rice genes (e.g., salt, tpi: McElroy et al., *Plant Cell* 2:163-171, 1990; Xu et al., *Plant Physiol.* 106:459-467, 1994). Similarly, introns from dicotyledonous plant genes such as petunia (e.g., rbcS), potato (e.g., st-ls1) and *Arabidopsis thaliana* (e.g., ubq3 and pat1) have been found to elevate gene expression rates (Dean et al., *Plant Cell* 1:201-208, 1989; Leon et al., *Plant Physiol.* 95:968-972, 1991; Norris et al., *Plant Mol Biol* 21:895-906, 1993; Rose and Last, *Plant J.*11:455-464, 1997). It has been shown that deletions or mutations within the splice sites of an intron reduce gene expression, indicating that splicing might be needed for IME (Mascarenhas et al., *Plant Mol Biol.* 15:913-920, 1990; Clancy and Hannah, *Plant Physiol.* 130:918-929, 2002). However, such splicing is not required for a certain IME in dicotyledonous plants, as shown by point mutations within the splice sites of the pat1 gene from *A. thaliana* (Rose and Beliakoff, *Plant Physiol.* 122:535-542, 2000).

Enhancement of gene expression by introns is not a general phenomenon because some intron insertions into recombinant expression cassettes fail to enhance expression (e.g., introns from dicot genes such as the rbcS gene from pea, the phaseolin gene from bean, and the stls-1 gene from *Solanum tuberosum*) and introns from maize genes (the ninth intron of the adh1 gene, and the first intron of the hsp81 gene) (Chee et al., *Gene* 41:47-57, 1986; Kuhlemeier et al., *Mol Gen Genet* 212:405-411, 1988; Mascarenhas et al., *Plant Mol. Biol.* 15:913-920, 1990; Sinibaldi and Mettler, In W E Cohn, K Moldave, eds, *Progress in Nucleic Acid Research and Molecular Biology*, Vol 42. Academic Press, New York, pp 229-257, 1992; Vancanneyt et al., *Mol. Gen. Genet.* 220:245-250, 1990). Therefore, not every intron can be employed to manipulate the gene expression level of non-endogenous genes or endogenous genes in transgenic plants. What characteristics or specific sequence features must be present in an intron sequence in order to enhance the expression rate of a given gene is not known in the prior art, and therefore it is not possible to predict whether a given plant intron, when used heterologously, will cause IME.

As used herein, the term "chimeric" refers to a single DNA molecule produced by fusing a first DNA molecule to a second DNA molecule, where neither the first nor second the DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments, for example the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is similar in composition, but not identical to, a first DNA molecule, and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" may also encompass a regulatory element having a nucleotide sequence comprising a substitution, deletion, and/or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial and plant cell transformation. In the present invention, a polynucleotide sequence provided as SEQ ID NOs:1, 2, 3, 4, 6, and 8 may be used to create variants that are similar in composition, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence, but the constituent elements comprising the chimeric regulatory element may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked. In the present invention, a polynucleotide sequence provided as SEQ ID NOs:1, 2, 3, 4, 6, and 8 provide a reference sequence wherein the constituent elements that comprise the reference sequence may be joined by methods known in the art and may comprise substitutions, deletions, and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule, where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. A vector according to the present invention may include an expression cassette or transgene cassette isolated from any of the aforementioned molecules. Expression cassettes or transgene cassettes useful in practicing the invention are comprised of the transcriptional regulatory expression element groups ("EXPs") presented as SEQ ID NOs:1, 6, or 8 operably linked to a heterologous coding sequence, which is operably linked to the 3' UTRs presented as SEQ ID NOs:10, 11, 12, or 13.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

Constructs of the present invention may be provided, in one embodiment, as double Ti plasmid border DNA constructs that have right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells that permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes a Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art (see, for example, *Molecular Cloning: A Laboratory Manual, 3$^{rd}$ edition Volumes* 1, 2, and 3, J. Sambrook, D. W. Russell, and N. Irwin, Cold Spring Harbor Laboratory Press, 2000). Methods for making recombinant vectors particularly suited to plant transformation include, without limitation, those described in U.S. Pat. Nos. 4,971, 908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, 1988; and Glick et al., *Methods in Plant Molecular Biology and Biotechnology*, CRC Press, Boca Raton, Fla., 1993). Typical vectors useful for expression of nucleic acids in higher plants are well known in the art and include vectors derived from the tumor-inducing (Ti) plasmid of *A. tumefaciens* (Rogers et al., *Methods in Enzymology* 153: 253-277, 1987). Other recombinant vectors useful for plant transformation, including the pCaMVCN transfer control vector, have also been described in the scientific literature (see, for example, Fromm et al., *Proc. Natl. Acad. Sci. USA* 82: 5824-5828, 1985).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus (CaMV) 35S transcript promoter (see, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOs:5, 7, and 9. Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively, immediately after 3' end of the splice site (AG) to eliminate the potential of unwanted start codons formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation (polyA tail). A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA*, 80: 4803-4807, 1983); wheat hsp17 3' region; pea rubisco small subunit 3' region; cotton E6 3' region (U.S. Pat. No. 6,096,950); 3' regions disclosed in WO/0011200 A2; and the coixin 3' UTR (U.S. Pat. No. 6,635,806).

3' UTRs typically find beneficial use for the recombinant expression of specific genes. In animal systems, machinery of 3' UTRs has been well defined (e.g. Zhao et al., *Microbiol Mol Biol Rev* 63:405-445, 1999; Proudfoot, *Nature* 322:562-565, 1986; Kim et al., *Biotechnology Progress* 19:1620-1622, 2003; Yonaha and Proudfoot, *EMBO J*. 19:3770-3777, 2000; Cramer et al., *FEBS Letters* 498:179-182, 2001; Kuerstem and Goodwin, *Nature Reviews Genetics* 4:626-637, 2003). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334, 2001. This may interfere with achieving adequate levels of expression, for instance in cases where strong gene expression from all cassettes is desired.

In plants, clearly defined polyadenylation signal sequences are not known. Hasegawa et al. (*Plant J*. 33:1063-1072, 2003) were not able to identify conserved polyadenylation signal sequences in both in vitro and in vivo systems in *Nicotiana sylvestris* and to determine the actual length of the primary (non-polyadenylated) transcript. A weak 3' UTR may generate read-through, which may affect the expression of the genes located in neighboring expression cassettes (Padidam and Cao, *BioTechniques* 31:328-334, 2001). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved sequences to enable easy prediction of an effective 3' UTR.

From a practical standpoint, it may be beneficial that a 3' UTR used in a transgene cassette possesses certain characteristics. For example, a 3' UTR useful in accordance with the present invention may efficiently and effectively terminate transcription of the transgene and prevent read-through of the transcript into any neighboring DNA sequence, which can be comprised of another transgene cassette, as in the case of multiple cassettes residing in one T-DNA, or the neighboring chromosomal DNA into which the T-DNA has been inserted. The 3' UTR optimally should not cause a reduction in the transcriptional activity imparted by the promoter, leader, and introns that are used to drive expression of the transgene. In plant biotechnology, the 3' UTR is often used for priming of amplification reactions of reverse transcribed RNA extracted from the transformed plant and may be used to (1) assess the transcriptional activity or expression of the transgene cassette once integrated into the plant chromosome; (2) assess the copy number of insertions within the plant DNA; and (3) assess zygosity of the resulting seed after breeding. The 3' UTR may also be used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower, or any other tissues derived from, for example, Big bluestem (*Andropogon gerardii*), Plume Grass [*Saccharum ravennae* (*Erianthus ravennae*)], Green bristlegrass (*Setaria viridis*), Teosinte (*Zea mays* subsp. *mexicana*), Foxtail millet (*Setaria italica*), or Coix (*Coix lacryma-jobi*). Using methods known to those skilled in the art, libraries of cDNA may be made from tissues isolated from a plant species using flower tissue, seed, leaf, root, or other plant tissues. The resulting cDNAs are sequenced using various sequencing methods known in the art. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence, as well as sequence derived from genomic DNA. A cDNA sequence may be used to design primers, which may then be used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library may be used to infer properties about patters of expression. For example, some 3' UTRs may be found in transcripts more abundant in root tissue rather than leaf tissue. This suggests that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types. 3' UTRs useful in practicing the invention are provided as SEQ ID NOs:9, 10, 11, and 12.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been show to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species, or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, in one embodiment of the present invention, a regulatory element, provided as SEQ ID NOs: 1, 2, 3, 4, 6, and 8, is operably linked to a transcribable polynucleotide molecule on order to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules in accordance with the present invention may be genes of agronomic interest. As used herein, the term "gene of agronomic interest" refers to a transcribable polynucleotide molecule that, when expressed in a particular plant tissue, cell, or cell type, confers a desirable characteristic, such as one associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent, such as an antisense or RNAi molecule targeting a particular gene for suppression. The product of a gene of agronomic interest may act within the plant in order to cause an effect upon the plant physiology or metabolism, or may be act as a pesticidal agent in the diet of a pest that feeds on the plant.

In one embodiment of the present invention, a promoter is incorporated into a construct such that the promoter is operably linked to a transcribable polynucleotide molecule that is a gene of agronomic interest. The expression of the gene of agronomic interest is desirable in order to confer an agronomically beneficial trait. Without limitation, a beneficial agronomic trait may include, for example, herbicide tolerance, insect control, modified yield, fungal disease resistance, virus resistance, nematode resistance, bacterial disease resistance, plant growth and development, starch production, modified oil production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production, among others. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716, 837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; and 6,476, 295), modified oil production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822, 141; 6,770,465; 6,706,950; 6,660,849; 6,596,538; 6,589, 767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; 5,958,745; and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding an RNA molecule that causes the targeted modulation of gene expression of an endogenous gene, for example via antisense (see for example, U.S. Pat. No. 5,107,065); inhibitory RNA ("RNAi," including modulation of gene expression via mechanisms mediated by miRNA, siRNA, trans-acting siRNA, and phased sRNA, e.g. as described in published applications US 2006/0200878 and US 2008/0066206, and in U.S. patent application Ser. No. 11/974,469); or cosuppression-mediated mechanisms. The RNA may also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231, 020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule may include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS, described in U.S. Pat. No. 5,599,670), green fluorescent protein and variants thereof (GFP, described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4), are well known in the art. Herbicides for which transgenic plant tolerance has been demonstrated and to which the method of the present invention can be applied, may include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and may include, but are not limited to, a transcribable polynucleotide molecule encoding 5-enolpyruvylshikimate-3-phosphate synthase (EPSPS for glyphosate tolerance, described in U.S. Pat. Nos. 5,627,061; 5,633,435; 6,040, 497; and 5,094,945); a transcribable polynucleotide molecule encoding a glyphosate oxidoreductase and a glyphosate-N-acetyl transferase (GOX, described in U.S. Pat. No. 5,463,175; GAT, described in U.S. Patent Publication No. 20030083480; and dicamba monooxygenase, described in U.S. Patent Publication No. 20030135879); a transcribable polynucleotide molecule encoding bromoxynil nitrilase (Bxn for Bromoxynil tolerance, described in U.S. Pat. No. 4,810,648); a transcribable polynucleotide molecule encoding phytoene desaturase (crtI) described in Misawa, et al. (*Plant Journal* 4:833-840, 1993; and *Plant Journal* 6:481-489, 1994) for norflurazon tolerance; a transcribable polynucleotide molecule encoding acetohydroxyacid synthase (AHAS, aka ALS) described in Sathasiivan, et al. (*Nucl. Acids Res.* 18:2188-2193, 1990) for tolerance to sulfonylurea herbicides; and the bar gene described in DeBlock, et al. (*EMBO Journal* 6:2513-2519, 1987) for glufosinate and bialaphos tolerance. The promoter molecules of the present invention may express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Selectable secreted marker proteins fall into a number of classes, including small, diffusible proteins which are detectable, (e.g. by ELISA), small active enzymes that are detectable in extracellular solution (e.g., alpha-amylase, beta-lactamase, phosphinothricin transferase), or proteins that are inserted or trapped in the cell wall (such as proteins that include a leader sequence such as that found in the expression unit of extension or tobacco pathogenesis related proteins, also known as tobacco PR-S). Other possible selectable marker genes will be apparent to those of skill in the art and are encompassed by the present invention.

Cell Transformation

The term "transformation" refers to the introduction of nucleic acid into a recipient host. As used herein, the term "host" refers to a bacterium, a fungus, or a plant, including any cells, tissue, organs, or progeny of the bacterium, fungus, or plant. For instance, a host cell according to the present invention may be any cell or organism, such as a plant cell, algae cell, algae, fungal cell, fungi, bacterial cell, insect cell, or the like. In an embodiment, hosts and transformed cells may include cells from: plants, *Aspergillus*, yeasts, insects, bacteria and algae. Plant tissues and cells of particular interest include, but are not limited to, protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacterium, fungus, or plant containing one or more heterologous polynucleic acid molecules.

There are many methods for introducing polynucleic acid molecules into plant cells. The method may generally comprise the steps of selecting a suitable host cell, transforming the host cell with a recombinant vector, and obtaining a transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205, 1991).

Technology for introduction of a DNA molecule into cells is well known to those of skill in the art. Methods and materials for transforming plant cells by introducing a plant DNA construct into a plant genome in the practice of this invention can include any of the well-known and demonstrated methods. Any transformation methods may be utilized to transform a host cell with one or more promoters and/or constructs of the present.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98, 1960; Simmonds, *Principles of crop improvement*, Longman, Inc., NY, 369-399, 1979; Sneep and Hendriksen, Plant breeding perspectives, Wageningen (ed), Center for Agricultural Publishing and Documentation, 1979; Fehr, *Soybeans: Improvement, Production and Uses*, 2nd Edition, Monograph, 16:249, 1987; Fehr, *Principles of variety development, Theory and Technique*, (Vol. 1) and *Crop Species Soybean* (Vol. 2), Iowa State Univ., Macmillan Pub. Co., NY, 360-376, 1987. Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The seeds of plants of this invention may be harvested from fertile transgenic plants and used to grow progeny generations of transformed plants of this invention, including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Regulatory Elements Isolated from Zea Mays and Corresponding Transcriptional Regulatory Expression Element Groups Regulatory elements were isolated from Zea mays, and transcriptional regulatory expression element group (EXP) sequences comprising the Zea mays regulatory elements were constructed.

Early planting of corn seeds as early as the beginning of April in Northern U.S. poses potentially detrimental risks to corn seeds. For example, prolonged cold and wet field conditions can prevent optimal germination and seedling establishment. Through transcript profiling and subsequent characterization, several candidate genes were identified that demonstrated a pattern of expression useful for the seed development and germination. The promoter and leader from a candidate gene, herein referred to as P-Zm.Nac-1:1:2 (SEQ ID NO:2) and L-Zm.Nac-1:1:1 (SEQ ID NO:4), respectively, were amplified from corn genomic DNA, and cloned and sequenced.

Amplification primers were designed based upon proprietary and public genomic and EST sequences, which were then used with GenomeWalker™ (Clontech Laboratories, Inc, Mountain View, Calif.) libraries constructed following the manufacturer's protocol to clone the 5' region of the corresponding genomic DNA sequence. Using this sequence, regulatory elements were bioinformatically identified within the 5' region for the gene. Using the results of this analysis, regulatory elements were defined within the 5' sequence upstream of the coding sequence of the gene. Primers were then designed to amplify the regulatory elements. The corresponding DNA molecule for each regulatory element was amplified using standard PCR conditions with primers containing unique restriction enzyme sites and genomic DNA isolated from Zea mays. This cloned sequence comprised the promoter and 5' UTR sequence upstream of the protein-coding region for the Zea mays gene. The resulting DNA fragment was ligated into base plant expression vectors using standard DNA cloning methods and sequenced.

Sequences of the identified transcriptional regulatory expression element groups ("EXPs") are provided herein as SEQ ID NOs:1, 6, and 8, as listed in Table 1 below. A promoter sequence is provided herein as SEQ ID NO:2. A leader sequence is provided herein as SEQ ID NO: 4. Intron sequences are provided herein as SEQ ID NOs: 5, 7, and 9.

TABLE 1

Transcriptional regulatory expression element groups ("EXPs"), promoter, leaders, and introns isolated from various grass species.

| Annotation | SEQ ID NO: | Description and/or regulatory elements of EXP linked in 5' to 3' direction |
|---|---|---|
| EXP-Zm.Nac + Zm.DnaK:1:1 | 1 | EXP: P-Zm.Nac-1:1:2 (SEQ ID NO: 2); L-Zm.Nac-1:1:1 (SEQ ID NO: 4); I-Zm.DnaK-1:1:1 (SEQ ID NO: 5) |
| P-Zm.Nac-1:1:2 | 2 | Promoter |
| P-Zm.Nac-1:1:2 + L-Zm.Nac-1:1:1 | 3 | Promoter + Leader |
| L-Zm.Nac-1:1:1 | 4 | Leader |
| I-Zm.DnaK-1:1:1 | 5 | Intron |
| EXP-Zm.Nac + Os.FBA:1:1 | 6 | EXP: P-Zm.Nac-1:1:2 (SEQ ID NO: 2); L-Zm.Nac-1:1:1 (SEQ ID NO: 4); I-Os.FBA-1-1:1:1 (SEQ ID NO: 6) |
| I-Os.FBA-1-1:1:1 | 7 | Intron |
| EXP-Zm.Nac + Os.Cab-1:1:1 | 8 | EXP: P-Zm.Nac-1:1:2 (SEQ ID NO: 2); L-Zm.Nac-1:1:1 (SEQ ID NO: 4); I-Os.Cab-1-1:1:1 (SEQ ID NO: 8) |
| I-Os.Cab-1-1:1:1 | 9 | Intron |

As shown in Table 1, for example, the transcriptional regulatory expression element group (EXP) designated EXP-Zm.Nac+Zm.DnaK:1:1 (SEQ ID NO:1), with components isolated from *Zea mays*, comprises a promoter element, P-Zm.Nac-1:1:2 (SEQ ID NO:2), operably linked 5' to a leader element, L-Zm.Nac-1:1:1 (SEQ ID NO:4), operably linked 5' to an intron element, I-Zm.DnaK-1:1:1 (SEQ ID NO:5). Other EXPs are linked similarly, as outlined in Table 1.

Example 2

Analysis of EXP-Zm.Nac+Zm.DnaK:1:1 (SEQ ID NO:1) Driving GUS in F1 Transgenic Corn Corn plants were transformed with the plant expression vector pMON73501, containing the transcriptional regulatory expression element group, EXP-Zm.Nac+Zm.DnaK: 1:1 (SEQ ID NO:1) driving expression of the β-glucuronidase (GUS) transgene, and the resulting plants were analyzed for GUS protein expression.

The EXP sequence was cloned into a plant binary transformation plasmid constructs using methods known in the art. The resulting plant expression plasmid construct, pMON73501, contained a right border region from *A. tumefaciens*, a first transgene cassette to test the transcriptional regulatory expression element group EXP-Zm.Nac+Zm.DnaK:1:1 (SEQ ID NO:1) operably linked to a coding sequence for β-glucuronidase (GUS, SEQ ID NO:14), operably linked 5' to the 3' UTR region T-AGRtu.nos-1:1:13 (SEQ ID NO:10); a second transgene selection cassette used for selection of transformed plant cells that confers resistance to the herbicide glyphosate driven by the CaMV 35S promoter, EXP-CaMV.35S:1:1 (SEQ ID NO:15), and a left border region from *A. tumefaciens*. The resulting plasmid was used to transform corn plants.

Corn plants were transformed with the GUS expression vector, pMON73501. $R_0$ generation transformants, selected for single copy insertions were crossed with non-transformed LH244 plants to produce an F1 population of transformants. GUS expression levels were measured in selected tissues over the course of development. The F1 tissues used for this study included: imbibed seed embryo, imbibed seed endosperm, root, and coleoptide at 3 days after germination (DAG); leaf and root at V3 stage; root and mature leaf at V7 stage; root, mature and senescing leaves, cob, silk, internode, anther, and pollen at VT stage (at tasseling, prior to reproduction); kernel 7 days after pollination (DAP) and; embryo and endosperm 21 and 35 DAP. Selected tissue samples were also analyzed for F1 plants exposed to conditions of drought and cold stress. V3 root and leaf tissue was sampled after cold and drought exposure, as well as two days after recovery from cold exposure (2 DAR).

Drought stress was induced in F1, V3 plants by withholding watering for 4 days allowing the water content to be reduced by at least 50% of the original water content of the fully watered plant. The drought protocol was comprised essentially of the following steps. V3 stage plants were deprived of water. As a corn plant experiences drought, the shape of the leaf will change from the usual healthy and unfolded appearance to a leaf demonstrating folding at the mid-rib vascular bundle and appearing V-shaped when viewed from the leaf tip to the stem. This change in morphology usually began to occur by approximately 2 days after the cessation of watering and was shown in earlier experiments to be associated with water loss of around 50% as measured by weight of pots prior to cessation of watering and weight of pots when the leaf curl morphology was observed in un-watered plants. Plants were considered to be under drought conditions, when the leaves showed wilting as evidenced by an inward curling (V-shape) of the leaf. This level of stress is considered to be a form of sub-lethal stress. Once each plant demonstrated drought induction as defined above, the plant was destroyed to acquire both root and leaf samples. Four plants for each vector were used and GUS measures taken as described below.

In addition to drought, F1 germinating seedlings and F1, V3 stage plants transformed with pMON73501 were also exposed to conditions of cold to determine if the regulatory elements demonstrated cold-induced expression of GUS. Sixty seeds derived from six seeds of each of 10 transformation events were tested for induction of gene expression under cold conditions. The seeds were germinated in Petri plates on water-saturated filter paper. Three days after germination, the seedlings were exposed to cold stress by placing the Petri dishes containing the germinated seedlings in a dark growth chamber set to 10° C. for 24 hours. At the end of the 24-hour period, the root and coleoptiles tissues were sampled for quantitative GUS expression as described below. Whole plants were tested for induction of GUS expression under cold stress at V3 stage. Twenty V3 stage corn plants, comprised of 2 plants from each of 10 transformation events, were exposed to a temperature of 12° C. in a growth chamber for 24 hours. Plants in the growth chamber were grown under a white light fluence of 800 μmoles/m$^2$·s with a light cycle of ten hours of white light and fourteen hours of darkness. After cold exposure, leaf and root tissues were sampled for quantitative GUS expression.

Histochemical GUS analysis was used for qualitative expression analysis of transformed plants. Whole tissue sections were incubated with GUS staining solution X-Gluc (5-bromo-4-chloro-3-indolyl-b-glucuronide) (1 mg/ml) for an appropriate length of time, rinsed, and visually inspected for blue coloration. GUS activity was qualitatively determined by direct visual inspection or inspection under a microscope using selected plant organs and tissues.

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 μl. Fluorescence was measured with excitation at 365 nm, emission at 445 nm, using a Fluoromax-3 (Horiba; Kyoto, Japan) with Micromax Reader, with slit width set at excitation 2 nm and emission 3 nm.

Table 2 below shows the mean level of GUS expression in selected tissues in F1 plants transformed with pMON73501.

TABLE 2

Mean GUS expression values of selected tissues and treatments of F1 generation transformed corn plants, transformed with pMON73501.

| Stages | Organ | Inducer | Mean | SE |
|---|---|---|---|---|
| Imbibed seed | Embryo | | 1730.43 | 260.50 |
| Imbibed seed | Endosperm | | 535.57 | 109.12 |
| 3 DAG | Root | | 290.78 | 65.98 |
| 3 DAG | Root | Cold | 250.15 | 46.41 |

TABLE 2-continued

Mean GUS expression values of selected tissues and treatments of F1 generation transformed corn plants, transformed with pMON73501.

| Stages | Organ | Inducer | Mean | SE |
|---|---|---|---|---|
| V3 | Root | | 295.14 | 74.69 |
| V3 | Root | Cold | 472.15 | 115.41 |
| V3 | Root | Cold 2 DAR | 104.04 | 25.67 |
| V3 | Root | Drought | 384.97 | 66.98 |
| V7 | Root | | 125.12 | 24.65 |
| VT | Root | | 57.80 | 13.56 |
| 3 DAG | Coleoptile | | 205.49 | 34.89 |
| 3 DAG | Coleoptile | Cold | 249.79 | 37.83 |
| V3 | Leaf | | 66.34 | 18.55 |
| V3 | Leaf | Cold | 290.51 | 89.09 |
| V3 | Leaf | Cold 2 DAR | 417.18 | 85.36 |
| V3 | Leaf | Drought | 120.23 | 35.30 |
| V7 | Leaf - Mature | | 45.60 | 10.66 |
| VT | Leaf - Mature | | 57.30 | 14.15 |
| VT | Leaf - Senescence | | 195.07 | 59.39 |
| VT | Cob | | 275.58 | 53.56 |
| VT | Silk | | 39.95 | 11.46 |
| VT | Internode | | 155.98 | 51.01 |
| VT | Anther | | 474.59 | 100.53 |
| VT | Pollen | | 35.06 | 24.11 |
| 21 DAP | Embryo | | 622.61 | 65.11 |
| 35 DAP | Embryo | | 1140.81 | 135.70 |
| 7 DAP | Kernel | | 350.35 | 20.28 |
| 21 DAP | Endosperm | | 684.27 | 64.73 |
| 35 DAP | Endosperm | | 738.38 | 96.71 |

As seen in Table 2, a striking feature with respect to expression driven by the EXP sequence, EXP-Zm.Nac+Zm.DnaK:1:1 (SEQ ID NO:1), comprising the promoter and leader P-Zm.Nac-1:1:2 (SEQ ID NO:2) and L-Zm.Nac-1:1:1 (SEQ ID NO: 4) was the higher level of expression observed in imbibed seed embryos and endosperm tissues relative to other tissues sampled. This high level of expression may confer advantages to germinating seeds expressing transgenes useful in providing protection against cold and wet stress conditions. Expression was also higher relative to the other tissues in the embryo and endosperm during early seed development (21 and 35 DAP). Such an expression pattern may also be advantageous for facilitating germination and growth of the resulting seed. For example, protein or products derived from the expression of transgenes operably linked to the Zea mays Nac promoter and leader expressed during the early stages of seed development would permit the accumulation of protein or derived products in the developing seed to be stored for rapid use upon germination in cold or wet conditions. Expression upon germination would provide additional advantages to the seed driving the desired transgenes by allowing for the expression of additional protein or derived product at a critical time under cold and wet stress conditions. A slight induction to cold was also observed in V3 leaf and root in this experiment.

Example 3

Analysis of Regulatory Elements Driving GUS in R0 Transgenic Corn

Corn plants were transformed with plant expression vectors containing EXP sequences driving expression of the β-glucuronidase (GUS) transgene, and the resulting plants were analyzed for GUS protein expression. The transcriptional regulatory expression element groups were cloned into plant binary transformation plasmid constructs using methods known in the art.

The resulting plant expression plasmid constructs contained a right border region from A. tumefaciens, a first transgene cassette to test the EXP sequence and 3' UTR combination comprised of an EXP sequence (indicated in Table 3), operably linked to a coding sequence for β-glucuronidase (GUS, SEQ ID NO:14), operably linked 5' to a 3' termination region (indicated in Table 3); a second transgene selection cassette used for selection of transformed plant cells that confers resistance to the herbicide glyphosate (CP4, U.S. RE39247, driven by the rice Actin 1 promoter, EXP-Os.Act1:1:1, SEQ ID NO:16), and a left border region from A. tumefaciens. The resulting plasmids were used to transform corn plants. Table 3 lists the plasmid designations, the transcriptional regulatory expression element groups, which are also described in Table 1, and the 3' UTRs that were placed in operable linkage with the GUS coding sequence. Each plasmid construct was comprised of a unique transgene cassette configuration comprised of specific introns and 3' UTRs placed in operably linkage with the promoter and leader P-Zm.Nac-1:1:2 (SEQ ID NO:2) and L-Zm.Nac-1:1:1 (SEQ ID NO:4).

TABLE 3

GUS plasmid constructs and corresponding transcriptional regulatory expression element groups and 3' UTRs.

| Plasmid Construct | Transcriptional Regulatory Expression Element Group | SEQ ID NO: | 3' UTR | SEQ ID NO: |
|---|---|---|---|---|
| pMON122713 | EXP-Zm.Nac + Os.FBA:1:1 | 6 | T-Os.Mth-1:1:1 | 12 |
| pMON122715 | EXP-Zm.Nac + Os.FBA:1:1 | 6 | T-Os.CLUS33428_1-1:1:1 | 11 |
| pMON127422 | EXP-Zm.Nac + Os.Cab-1:1:1 | 8 | T-Os.Ara5-1:1:1 | 13 |
| pMON128892 | EXP-Zm.Nac + Os.Cab-1:1:1 | 8 | T-Os.Mth-1:1:1 | 12 |

Plants were transformed using Agrobacterium-mediated transformation methods known in the art. Histochemical and quantitative GUS analysis was performed as described in Example 2 above. The average $R_0$ GUS expression observed for each GUS transgene cassette transformed in corn plants is presented in Table 4 below.

TABLE 4

Average R₀ GUS expression in root and leaf tissue.

| Stage | Organ | Mean GUS Expression | | | |
|---|---|---|---|---|---|
| | | pMON122713 | pMON122715 | pMON127422 | pMON128892 |
| V3 | Leaf | nd | 128.28 | 65.73 | nd |
| | Root | nd | 73.61 | nd | nd |
| V4 | Leaf | 7.47 | Nd | nd | 261.38 |
| | Root | 3.15 | Nd | nd | nd |
| V7 | Leaf | nd | 110.47 | 34.18 | 68.43 |
| | Root | nd | 11.17 | 5.57 | nd |
| VT | Leaf | 5.81 | 42.23 | 87.04 | 102.55 |
| | Root | 2.02 | 26.34 | 1.16 | 20.76 |
| | Anthers | 20.45 | 115.86 | 22.47 | 145.84 |
| VT/R1 | Silk | 46.33 | 18.63 | 97.14 | nd |
| R3 | 21DAP-Embryo | 229.75 | 165.29 | 385.4 | 220.5 |
| | 21DAP-Endosperm | 40.47 | 215.04 | 192.02 | 223.77 |

Consistent with the results obtained in Example 2, Table 4 shows that expression was highest in the developing embryo (21 DAP) for all four of the transgene cassettes. FIG. 1 illustrates the different patterns of expression that were conferred by each transgene cassette configuration. Expression in the developing embryo was highest for the transgene cassette comprised of EXP sequence, EXP-Zm-.Nac+Os.Cab-1:1:1 (SEQ ID NO:8), which was operably linked to the 3′ UTR, T-Os.Ara5-1:1:1 (SEQ ID NO:13) with respect to the other three transgene cassettes. Similar levels of expression were observed in the developing embryo and endosperm of plants transformed with the expression cassette comprised of the transcriptional regulatory expression element group, EXP-Zm.Nac+Os.Cab-1:1:1 (SEQ ID NO:8), which was operably linked to the 3′ UTR, T-Os.Mth-1:1:1 (SEQ ID NO:12). For the transgene cassette comprised of the transcriptional regulatory expression element group, EXP-Zm.Nac+Os.FBA:1:1 (SEQ ID NO:6), which was operably linked to the 3′ UTR, T-Os.Mth-1:1:1 (SEQ ID NO:12), expression in the endosperm was much lower relative to the expression in the embryo. For the transgene cassette comprised of the transcriptional regulatory expression element group, EXP-Zm.Nac+Os.FBA:1:1 (SEQ ID NO:6), which was operably linked to the 3′ UTR, T-Os-.CLUS33428_1-1:1:1 (SEQ ID NO:11), expression in the embryo was lower relative to the expression in the endosperm. Each transgene cassette configuration provided a unique pattern of expression in the developing R₀ seed.

Figure 2:
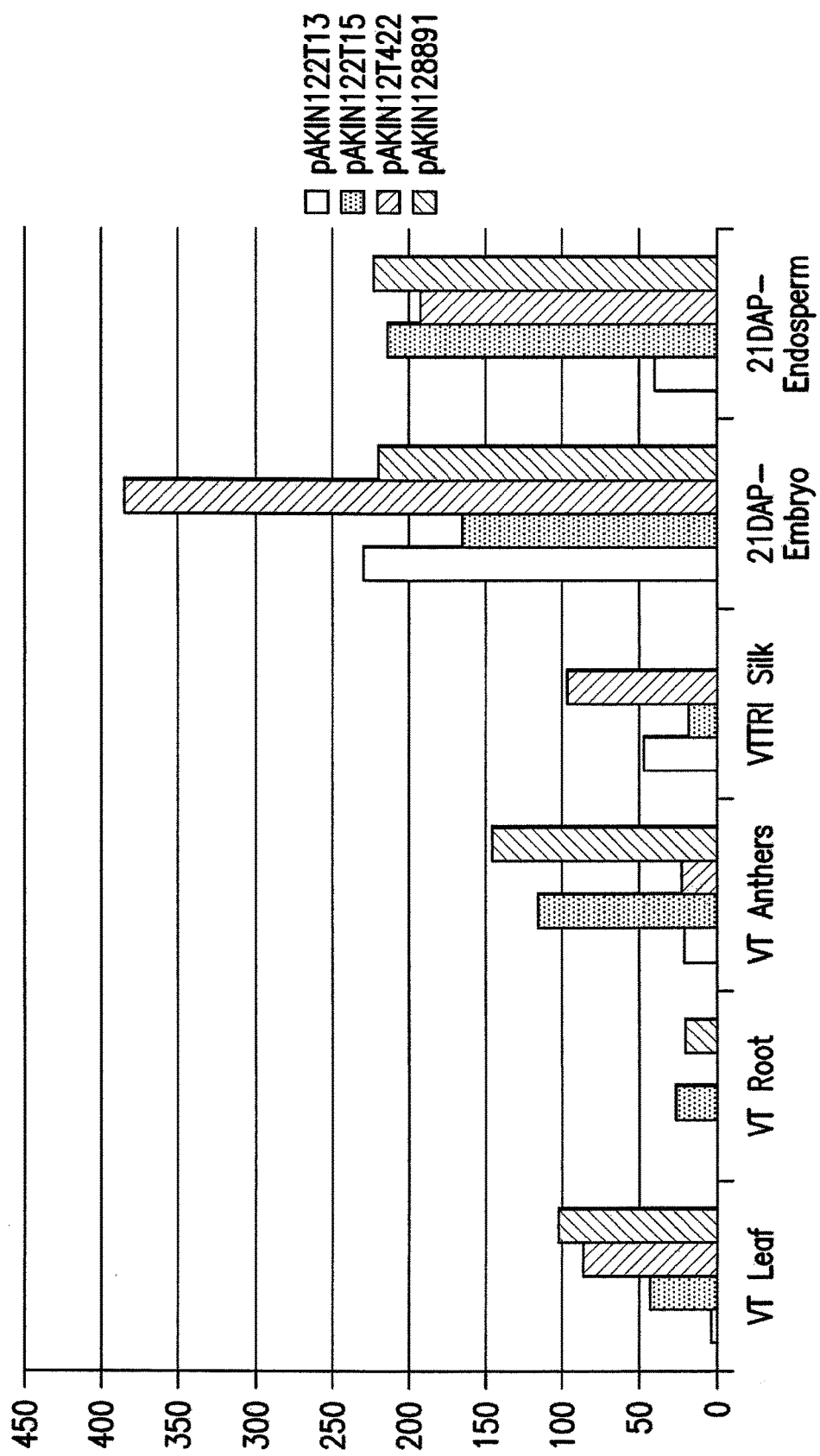
FIG. 2—shows β-glucuronidase (GUS) expression in selected tissues of transgenic corn imparted by different transgene cassette configurations. Each transgene cassette configuration is comprised of the GUS coding sequence operably linked to the transcriptional regulatory expression element groups EXP-Zm.Nac+Os.FBA:1:1 (SEQ ID NO:6) and EXP.-Zm.Nac+Os.Cab-1:1:1 (SEQ ID NO:8), and the 3' UTRs T-Os.CLUS33428_1-1:1:1 (SEQ ID NO:11), T-Os-.Mth-1:1:1 (SEQ ID NO:12), and T-Os.AraS-1:1:1. (SEQ II) NO:13), as shown in Table 4 of Example 3.

Expression differences in the root, leaf, anther, and silk, as well as the developing seed of plants transformed with the four different transgene cassettes, was also observed. FIG. 2 illustrates the different patterns of expression that were conferred by each transgene cassette configuration in each of the above described tissues. For example, leaf expression was higher in those transgene cassettes comprised of the EXP sequence, EXP-Zm.Nac+Os.Cab-1:1:1 (SEQ ID NO:8) relative to the transgene cassettes comprising EXP-Zm-.Nac+Os.FBA:1:1 (SEQ ID NO:6). Anther expression was higher in the two transgene cassettes comprised of the transcriptional regulatory expression element group, EXP-Zm.Nac+Os.FBA:1:1 (SEQ ID NO:6), which was operably linked to the 3′ UTR, T-Os.CLUS33428_1-1:1:1 (SEQ ID NO:11) and the transcriptional regulatory expression element group, EXP-Zm.Nac+Os.Cab-1:1:1 (SEQ ID NO:8), which was operably linked to the 3′ UTR, T-Os.Mth-1:1:1 (SEQ ID NO:12). Each of the four transgene cassette configurations provided unique expression patterns in the R₀ transformants.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A DNA molecule comprising a DNA sequence selected from the group consisting of:
   a) a sequence with at least 98 percent sequence identity to SEQ ID NO: 1, wherein the sequence has promoter activity;
   b) a sequence comprising SEQ ID NO: 1; and
   c) a fragment of SEQ ID NO: 1 comprising SEQ ID NO: 2, wherein the fragment has promoter activity;
   wherein said sequence is operably linked to a heterologous transcribable polynucleotide molecule.

2. The DNA molecule of claim 1, wherein the DNA sequence comprises promoter activity.

3. The DNA molecule of claim 1, wherein the heterologous transcribable polynucleotide molecule comprises a gene of agronomic interest.

4. The DNA molecule of claim 3, wherein the gene of agronomic interest confers herbicide tolerance in plants.

5. The DNA molecule of claim 3, wherein the gene of agronomic interest confers pest resistance in plants.

6. A transgenic plant cell comprising a heterologous DNA molecule comprising a sequence selected from the group consisting of:
   a) a sequence with at least 98 percent sequence identity to SEQ ID NO: 1, wherein the sequence has promoter activity;
   b) a sequence comprising SEQ ID NO: 1; and
   c) a fragment of SEQ ID NO: 1 comprising SEQ ID NO: 2, wherein the fragment has promoter activity;
   wherein said sequence is operably linked to a heterologous transcribable polynucleotide molecule.

7. The transgenic plant cell of claim 6, wherein said transgenic plant cell is a monocotyledonous plant cell.

8. The transgenic plant cell of claim 6, wherein said transgenic plant cell is a dicotyledonous plant cell.

9. A transgenic plant, or part thereof, comprising the DNA molecule of claim 1.

10. A progeny plant of the transgenic plant of claim 9, or a part thereof, wherein the progeny plant or part thereof comprises said DNA molecule.

11. A transgenic seed, wherein the seed comprises the DNA molecule of claim 1.

12. A method of producing a commodity product comprising obtaining a transgenic plant or part thereof according to claim 9 and producing the commodity product therefrom.

13. The method of claim 12, wherein the commodity product is protein concentrate, protein isolate, grain, starch, seeds, meal, flour, biomass, or seed oil.

14. A method of expressing a transcribable polynucleotide molecule comprising obtaining a transgenic plant according to claim 9 and cultivating plant, wherein the transcribable polynucleotide is expressed.

* * * * *

SEQUENCE LISTING

```
<160> NUMBER OF SEQ ID NOS: 16

<210> SEQ ID NO 1
<211> LENGTH: 2305
<212> TYPE: DNA
<213> ORGANISM: Artificial sequence
<220> FEATURE:
<223> OTHER INFORMATION: Chimeric transcriptional regulatory expression
      element group

<400> SEQUENCE: 1
gaggtgcata aggctggcaa gacgacagtt aggaacgcat gcgagcgagg ttgacggacg        60
cgataaggtt agcgcatgcg tcgaacgcgg gctggcgagg gtggaaggca tgataaggct       120
```

```
attgggtagc gcaaaatgtg tagacagcgg gcgagtgagg atggcagtgg tggcatgcat    180
ggacgcggtt ggagcatacg cgacaagaat ggagcacgac gtagatttcg ggaggccgtg    240
gttggagcgc ccgcgggcga gatggcggcc atggttagag cgcccgtggt tacgggtggg    300
ttcatggcga gcggaggggt tgcaagattt ccaggcgct cgggtcggtt gcaagctcca     360
cggtggaggc gtgacggaga cgacgtgggg agggaggtcg tggggaaatt cggacgagca    420
gaggcgtggc aggtgtggca tggggaggga ggtcgcgggg agggcgcagg gaggtggcat    480
ggggagggag gctggggacg aagatgatgt gggcccagag ggacgcggga caaagaattg    540
cgtatgataa cgggttgatt cgtagaattt taggcggtat ttataaaaat gacgcaggac    600
agccattggt actgatactt taatatagta gagaagagat ataaattagg acgggtacaa    660
caagaccaca cgtactaaca ttttttttg tcacaggctg ctctaataca tatctctatg      720
ataagcgagc tagggatgct agcgtgtcca tttgattcct atataaatct ccaattatag    780
ctgtagcaat taatttaata aacacccaac aatagatcaa atctcatagc aaatcataat    840
catgaatgct ccaaaatcag ctagctggct ctcccttatc ttcgtttttc cttcttctcc    900
tgcaacgaaa agaaaaaaaa agaaaagaaa agaaaacggc cgcttgtggt actaactccc    960
aactacgcac ctaccgcgcg cataactctt ggccgcctgc cctcatcacc tccgcgtcgc   1020
cgtcgactca tccttatcct ccccatcacg ctcaccccgc gcccgcaccg cgccatccgt   1080
actttccccgg ccgccccacc gctggccgcc ccgacgtgtc gcgccgccac cggaaggtcc  1140
cgggccgtcg gcgggcaga gcgcctgcag cggtggaccc acgccacgct gacgcgggcg    1200
cgcgtccgtc caagaaacct gacgtaagca gtgacagaat tggcgccgcc tctcggcgtc   1260
cacgtgtcgt ggtcaaccctg tcagagtggg gctccgtgtg tgcgctaccg caggggcccg  1320
gcgcacgggc cacacgtgtc gcggtcgacc gcggctataa atgcccggct ccgcactcgg   1380
aacaagtttc aagctctcct cccctcttcc taccattagc agtagccaca gccagaacac   1440
cagcagacag cagcatcagc agggaggaac acctcgaggc ctcggactag tcgagagatc   1500
taccgtcttc ggtacgcgct cactccgccc tctgcctttg ttactgccac gtttctctga   1560
atgctctctt gtgtggtgat tgctgagagt ggtttagctg gatctagaat tacactctga   1620
aatcgtgttc tgcctgtgct gattacttgc cgtcctttgt agcagcaaaa tataggggaca 1680
tggtagtacg aaacgaagat agaacctaca cagcaatacg agaaatgtgt aatttggtgc   1740
ttagcggtat ttatttaagc acatgttggt gttatagggc acttggattc agaagtttgc   1800
tgttaattta ggcacaggct tcatactaca tgggtcaata gtatagggat tcatattata   1860
ggcgatacta taataatttg ttcgtctgca gagcttatta tttgccaaaa ttagatattc   1920
ctattctgtt tttgtttgtg tgctgttaaa ttgttaacgc ctgaaggaat aaatataaat   1980
gacgaaattt tgatgtttat ctctgctcct ttattgtgac cataagtcaa gatcagatgc   2040
acttgttta aatattgttg tctgaagaaa taagtactga cagtattttg atgcattgat    2100
ctgcttgttt gttgtaacaa aatttaaaaa taaagagttt ccttttgtt gctctcctta     2160
cctcctgatg gtatctagta tctaccaact gacactatat tgcttctctt tacatacgta   2220
tcttgctcga tgccttctcc ctagtgttga ccagtgttac tcacatagtc tttgctcatt   2280
tcattgtaat gcagatacca agcgg                                         2305
```

<210> SEQ ID NO 2
<211> LENGTH: 1386
<212> TYPE: DNA
<213> ORGANISM: Zea mays

<400> SEQUENCE: 2

```
gaggtgcata aggctggcaa gacgacagtt aggaacgcat gcgagcgagg ttgacggacg    60
cgataaggtt agcgcatgcg tcgaacgcgg gctggcgagg gtggaaggca tgataaggct   120
attgggtagc gcaaaatgtg tagacagcgg gcgagtgagg atggcagtgg tggcatgcat   180
ggacgcggtt ggagcatacg cgacaagaat ggagcacgac gtagatttcg ggaggccgtg   240
gttggagcgc ccgcgggcga gatggcggcc atggttagag cgcccgtggt tacgggtggg   300
ttcatggcga gcggaggggt tgcaagattt ccagggcgct cgggtcggtt gcaagctcca   360
cggtggaggc gtgacggaga cgacgtgggg agggaggtcg tggggaaatt cggacgagca   420
gaggcgtggc aggtgtggca tggggaggga ggtcgcgggg agggcgcagg gaggtggcat   480
ggggagggag gctggggacg aagatgatgt gggcccagag ggacgcggga caaagaattg   540
cgtatgataa cgggttgatt cgtagaattt taggcggtat ttataaaaat gacgcaggac   600
agccattggt actgatactt taatatagta gagaagagat ataaattagg acgggtacaa   660
caagaccaca cgtactaaca ttttttttttg tcacaggctg ctctaataca tatctctatg   720
ataagcgagc tagggatgct agcgtgtcca tttgattcct atataaatct ccaattatag   780
ctgtagcaat taatttaata aacacccaac aatagatcaa atctcatagc aaatcataat   840
catgaatgct ccaaaatcag ctagctggct ctcccttatc ttcgtttttc cttcttctcc   900
tgcaacgaaa agaaaaaaaa agaaaagaaa agaaaacggc cgcttgtggt actaactccc   960
aactacgcac ctaccgcgcg cataactctt ggccgcctgc cctcatcacc tccgcgtcgc  1020
cgtcgactca tccttatcct ccccatcacg ctcaccccgc gcccgcaccg cgccatccgt  1080
actttcccgg ccgccccacc gctggccgcc ccgacgtgtc gcgccgccac cggaaggtcc  1140
cgggccgtcg ggcgggcaga gcgcctgcag cggtggaccc acgccacgct gacgcgggcg  1200
cgcgtccgtc caagaaacct gacgtaagca gtgacagaat tggcgccgcc tctcggcgtc  1260
cacgtgtcgt ggtcaacctg tcagagtggg gctccgtgtg tgcgctaccg caggggcccg  1320
gcgcacgggc cacacgtgtc gcggtcgacc gcggctataa atgcccggct ccgcactcgg  1380
aacaag                                                            1386
```

<210> SEQ ID NO 3
<211> LENGTH: 1471
<212> TYPE: DNA
<213> ORGANISM: Zea mays

<400> SEQUENCE: 3

```
gaggtgcata aggctggcaa gacgacagtt aggaacgcat gcgagcgagg ttgacggacg    60
cgataaggtt agcgcatgcg tcgaacgcgg gctggcgagg gtggaaggca tgataaggct   120
attgggtagc gcaaaatgtg tagacagcgg gcgagtgagg atggcagtgg tggcatgcat   180
ggacgcggtt ggagcatacg cgacaagaat ggagcacgac gtagatttcg ggaggccgtg   240
gttggagcgc ccgcgggcga gatggcggcc atggttagag cgcccgtggt tacgggtggg   300
ttcatggcga gcggaggggt tgcaagattt ccagggcgct cgggtcggtt gcaagctcca   360
cggtggaggc gtgacggaga cgacgtgggg agggaggtcg tggggaaatt cggacgagca   420
gaggcgtggc aggtgtggca tggggaggga ggtcgcgggg agggcgcagg gaggtggcat   480
ggggagggag gctggggacg aagatgatgt gggcccagag ggacgcggga caaagaattg   540
cgtatgataa cgggttgatt cgtagaattt taggcggtat ttataaaaat gacgcaggac   600
```

```
agccattggt actgatactt taatatagta gagaagagat ataaattagg acgggtacaa      660
caagaccaca cgtactaaca ttttttttg tcacaggctg ctctaataca tatctctatg       720
ataagcgagc tagggatgct agcgtgtcca tttgattcct atataaatct ccaattatag     780
ctgtagcaat taatttaata aacacccaac aatagatcaa atctcatagc aaatcataat     840
catgaatgct ccaaaatcag ctagctggct ctcccttatc ttcgttttc cttcttctcc      900 tgcaacgaaa agaaaaaaaa agaaaagaaa agaaaacggc cgcttgtggt actaactccc    960
aactacgcac ctaccgcgcg cataactctt ggccgcctgc cctcatcacc tccgcgtcgc    1020
cgtcgactca tccttatcct ccccatcacg ctcaccccgc gcccgcaccg cgccatccgt    1080
actttcccgg ccgccccacc gctggccgcc ccgacgtgtc gcgccgccac cggaaggtcc    1140
cgggccgtcg gcgcgggcaga gcgcctgcag cggtggaccc acgccacgct gacgcgggcg   1200
cgcgtccgtc caagaaacct gacgtaagca gtgacagaat tggcgccgcc tctcggcgtc    1260
cacgtgtcgt ggtcaacctg tcagagtggg gctccgtgtg tgcgctaccg cagggggccg    1320
gcgcacgggc cacacgtgtc gcggtcgacc gcggctataa atgcccggct ccgcactcgg    1380
aacaagtttc aagctctcct cccctcttcc taccattagc agtagccaca gccagaacac    1440
cagcagacag cagcatcagc agggaggaac a                                   1471

<210> SEQ ID NO 4
<211> LENGTH: 85
<212> TYPE: DNA
<213> ORGANISM: Zea mays

<400> SEQUENCE: 4
tttcaagctc tcctcccctc ttcctaccat tagcagtagc cacagccaga acaccagcag     60
acagcagcat cagcagggag gaaca                                          85

<210> SEQ ID NO 5
<211> LENGTH: 804
<212> TYPE: DNA
<213> ORGANISM: Zea mays

<400> SEQUENCE: 5
accgtcttcg gtacgcgctc actccgccct ctgcctttgt tactgccacg tttctctgaa     60
tgctctcttg tgtggtgatt gctgagagtg gtttagctgg atctagaatt acactctgaa   120
atcgtgttct gcctgtgctg attacttgcc gtcctttgta gcagcaaaat atagggacat   180
ggtagtacga aacgaagata gaacctacac agcaatacga gaaatgtgta atttggtgct   240
tagcggtatt tatttaagca catgttggtg ttatagggca cttggattca gaagtttgct   300
gttaatttag gcacaggctt catactacat gggtcaatag tatagggatt catattatag   360
gcgatactat aataaatttgt tcgtctgcag agcttattat ttgccaaaat tagatattcc   420
tattctgttt tgtttgtgt gctgttaaat tgttaacgcc tgaaggaata aatataaatg    480
acgaaatttt gatgtttatc tctgctcctt tattgtgacc ataagtcaag atcagatgca   540
cttgttttaa atattgttgt ctgaagaaat aagtactgac agtatttga tgcattgatc    600 tgcttgtttt ttgtaacaaa atttaaaaat aaagagtttc ctttttgttg ctctccttac  660
ctcctgatgg tatctagtat ctaccaactg acactatatt gcttctcttt acatacgtat   720
cttgctcgat gccttctccc tagtgttgac cagtgttact cacatagtct ttgctcattt   780
cattgtaatg cagataccaa gcgg                                           804
```

<210> SEQ ID NO 6
<211> LENGTH: 2232
<212> TYPE: DNA
<213> ORGANISM: Artificial sequence
<220> FEATURE:
<223> OTHER INFORMATION: Chimeric transcriptional regulatory expression
      element group

<400> SEQUENCE: 6

| | | | | | | |
|---|---|---|---|---|---|---|
| gaggtgcata | aggctggcaa | gacgacagtt | aggaacgcat | gcgagcgagg | ttgacggacg | 60 |
| cgataaggtt | agcgcatgcg | tcgaacgcgg | gctggcgagg | gtggaaggca | tgataaggct | 120 |
| attgggtagc | gcaaaatgtg | tagacagcgg | gcgagtgagg | atggcagtgg | tggcatgcat | 180 |
| ggacgcggtt | ggagcatacg | cgacaagaat | ggagcacgac | gtagatttcg | ggaggccgtg | 240 |
| gttggagcgc | ccgcgggcga | gatggcggcc | atggttagag | cgcccgtggt | tacgggtggg | 300 |
| ttcatggcga | gcggaggggt | tgcaagattt | ccagggcgct | cgggtcggtt | gcaagctcca | 360 |
| cggtggaggc | gtgacggaga | cgacgtgggg | agggaggtcg | tggggaaatt | cggacgagca | 420 |
| gaggcgtggc | aggtgtggca | tggggaggga | ggtcgcgggg | agggcgcagg | gaggtggcat | 480 |
| ggggagggag | gctggggacg | aagatgatgt | gggcccagag | ggacgcggga | caaagaattg | 540 |
| cgtatgataa | cggttgatt | cgtagaattt | taggcggtat | ttataaaaat | gacgcaggac | 600 |
| agccattggt | actgatactt | taatatagta | gagaagagat | ataaattagg | acgggtacaa | 660 |
| caagaccaca | cgtactaaca | ttttttttg | tcacaggctg | ctctaataca | tatctctatg | 720 |
| ataagcgagc | tagggatgct | agcgtgtcca | tttgattcct | atataaatct | ccaattatag | 780 |
| ctgtagcaat | taatttaata | aacacccaac | aatagatcaa | atctcatagc | aaatcataat | 840 |
| catgaatgct | ccaaaatcag | ctagctggct | ctcccttatc | ttcgttttc | cttcttctcc | 900 |
| tgcaacgaaa | agaaaaaaa | agaaaagaaa | agaaaacggc | cgcttgtggt | actaactccc | 960 |
| aactacgcac | ctaccgcgcg | cataactctt | ggccgcctgc | cctcatcacc | tccgcgtcgc | 1020 |
| cgtcgactca | tccttatcct | ccccatcacg | ctcaccccgc | gcccgcaccg | cgccatccgt | 1080 |
| actttcccgg | ccgccccacc | gctggccgcc | ccgacgtgtc | gcgccgccac | cggaaggtcc | 1140 |
| cgggccgtcg | ggcgggcaga | gcgcctgcag | cggtggaccc | acgccacgct | gacgcgggcg | 1200 |
| cgcgtccgtc | caagaaacct | gacgtaagca | gtgacagaat | tggcgccgcc | tctcggcgtc | 1260 |
| cacgtgtcgt | ggtcaacctg | tcagagtggg | gctccgtgtg | tgcgctaccg | caggggcccg | 1320 |
| gcgcacgggc | cacacgtgtc | gcggtcgacc | gcggctataa | atgcccggct | ccgcactcgg | 1380 |
| aacaagtttc | aagctctcct | cccctcttcc | taccattagc | agtagccaca | gccagaacac | 1440 |
| cagcagacag | cagcatcagc | agggaggaac | acctgcaggc | ctacgctgac | aagctgactc | 1500 |
| tagcagatcc | tctagaacca | tcttccacac | actcaagcca | cactattgga | gaacacacag | 1560 |
| ggacaacaca | ccataagatc | tcaagaccgc | ggtatgcttt | ctgaatatca | tccgtactgt | 1620 |
| tctatggttt | ttggcatgca | tttgtttcct | ctttatatca | atgacaagtg | aaggaacttt | 1680 |
| atgtagtttt | atgatagata | taagcacttt | atcgtcagga | aatcaaatag | gatgtgcagt | 1740 |
| caagctaagt | tatatatagc | agaattcagt | gaacataaaa | cacttgtttt | gatataacat | 1800 |
| gattcaaata | tactggcatc | tctagttcaa | atctactctt | caaagttata | taatgcattt | 1860 |
| gaaggaaaat | ttctatcttc | aacttcacag | aaagcaaaat | agatatgatt | tgtgtatacc | 1920 |
| aaatgaactt | agagactcaa | aatatactag | taatacattt | gtaaactcga | catctgcatc | 1980 |
| aagacatgac | atgggttaac | cactagcagt | tgtaaggata | aagcatgaag | cattcatgtg | 2040 |
| tcctgcttat | gttctatgaa | ccatctgcag | gtcataattc | agaagaaaag | tttggaactt | 2100 |

```
ctaatcctac aacataacaa gcatactttt atcaactttg gataataaat tcttaagatg    2160 agttttttcat tcaattatgg ttcagaacta gaagattaaa aactttatcc ttcttgctgt    2220
agaaaaccat tg                                                         2232
```

<210> SEQ ID NO 7
<211> LENGTH: 651
<212> TYPE: DNA
<213> ORGANISM: Oryza sativa

<400> SEQUENCE: 7

```
caagaccgcg gtatgctttc tgaatatcat ccgtactgtt ctatggtttt tggcatgcat      60
ttgtttcctc tttatatcaa tgacaagtga aggaacttta tgtagtttta tgatagatat     120
aagcacttta tcgtcaggaa atcaaatagg atgtgcagtc aagctaagtt atatatagca     180
gaattcagtg aacataaaac acttgttttg ataacatg attcaaatat actggcatct      240
ctagttcaaa tctactcttc aaagttatat aatgcatttg aaggaaaatt tctatcttca     300
acttcacaga aagcaaaata gatatgattt gtgtatacca aatgaactta gagactcaaa     360
atatactagt aatacatttg taaactcgac atctgcatca agacatgaca tgggttaacc     420
actagcagtt gtaaggataa agcatgaagc attcatgtgt cctgcttatg ttctatgaac     480
catctgcagg tcataattca aagaaaagt ttggaacttc taatcctaca acataacaag      540
catactttta tcaactttgg ataataaatt cttaagatga gttttcatt caattatggt      600 tcagaactag aagattaaaa actttatcct tcttgctgta gaaaaccatt g              651
```

<210> SEQ ID NO 8
<211> LENGTH: 1629
<212> TYPE: DNA
<213> ORGANISM: Artificial sequence
<220> FEATURE:
<223> OTHER INFORMATION: Chimeric transcriptional regulatory expression element group

<400> SEQUENCE: 8

```
gaggtgcata aggctggcaa gacgacagtt aggaacgcat gcgagcgagg ttgacggacg      60
cgataaggtt agcgcatgcg tcgaacgcgg gctggcgagg gtggaaggca tgataaggct     120
attgggtagc gcaaaatgtg tagacagcgg gcgagtgagg atggcagtgg tggcatgcat     180
ggacgcggtt ggagcatacg cgacaagaat ggagcacgac gtagatttcg ggaggccgtg     240
gttggagcgc ccgcgggcga gatggcggcc atggttagag cgcccgtggt tacgggtggg     300
ttcatggcga gcggaggggt tgcaagattt ccagggcgct cgggtcggtt gcaagctcca     360
cggtggaggc gtgacggaga cgacgtgggg agggaggtcg tggggaaatt cggacgagca     420
gaggcgtggc aggtgtggca tggggaggga ggtcgcgggg agggcgcagg gaggtggcat     480
ggggagggag gctggggacg aagatgatgt gggcccagag ggacgcggga caaagaattg     540
cgtatgataa cgggttgatt cgtagaattt taggcggtat ttataaaaat gacgcaggac     600
agccattggt actgatactt taatatagta gagaagagat ataaattagg acgggtacaa     660
caagaccaca cgtactaaca ttttttttg tcacaggctg ctctaataca tatctctatg     720
ataagcgagc tagggatgct agcgtgtcca tttgattcct atataaatct ccaattatag     780
ctgtagcaat taattaata aacacccaac aatagatcaa atctcatagc aaatcataat     840
catgaatgct ccaaaatcag ctagctggct ctcccttatc ttcgttttc cttcttctcc     900 tgcaacgaaa agaaaaaaaa agaaaagaaa agaaaacggc cgcttgtggt actaactccc     960
```

```
aactacgcac ctaccgcgcg cataactctt ggccgcctgc cctcatcacc tccgcgtcgc    1020
cgtcgactca tccttatcct ccccatcacg ctcaccccgc gcccgcaccg cgccatccgt    1080
actttcccgg ccgccccacc gctggccgcc ccgacgtgtc gcgccgccac cggaaggtcc    1140
cgggccgtcg ggcgggcaga gcgcctgcag cggtggaccc acgccacgct gacgcgggcg    1200
cgcgtccgtc caagaaacct gacgtaagca gtgacagaat tggcgccgcc tctcggcgtc    1260
cacgtgtcgt ggtcaacctg tcagagtggg gctccgtgtg tgcgctaccg caggggcccg    1320
gcgcacgggc cacacgtgtc gcggtcgacc gcggctataa atgcccggct ccgcactcgg    1380
aacaagtttc aagctctcct cccctcttcc taccattagc agtagccaca gccagaacac    1440
cagcagacag cagcatcagc agggaggaac acctgcaggc ctacacgctg acaagctgac    1500
tctagcagat ctccctgcca aggtatatat gctgattgat ttctactctt cctcaattca    1560
aaattgaaag atattatgct gatctggtta aatttatgtt tggtttggtt tggtttcagc    1620
aaggtgctg                                                           1629

<210> SEQ ID NO 9
<211> LENGTH: 117
<212> TYPE: DNA
<213> ORGANISM: Oryza sativa

<400> SEQUENCE: 9
ccctgccaag gtatatatgc tgattgattt ctactcttcc tcaattcaaa attgaaagat     60
attatgctga tctggttaaa tttatgtttg gtttggtttg gtttcagcaa ggtgctg       117

<210> SEQ ID NO 10
<211> LENGTH: 253
<212> TYPE: DNA
<213> ORGANISM: Agrobacterium tumefaciens

<400> SEQUENCE: 10
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggttttttatg attagagtcc cgcaattata catttaatac    180
gcgatagaaa acaaaatata gcgcgcaaac taggataaat tatcgcgcgc ggtgtcatct    240
atgttactag atc                                                      253

<210> SEQ ID NO 11
<211> LENGTH: 380
<212> TYPE: DNA
<213> ORGANISM: Oryza sativa

<400> SEQUENCE: 11
tcgatcaatc gatcacgtcg tcgtctcggc tcgtcatcaa tcgcgatcga tcggtcgttt     60
tcacctaata ataatataat catatgtgtg tgtgcaaaga ataacgaatt aacctccccca    120 agcttcatgt atgcatacat gcatcgttag tgcatgtgtc cctgatcatg ggtctctggg    180
ggaggatcat gttgtgtcgt gtgtcggctg tgtctcggtt atcgtcttat cgatttcgat    240
catatcggcc aattgttgtc gcgctggcca cgtatatgta cttgatcgat gaccgagaaa    300
ctcctaggtc aatctgtgtg ttcatatata catcagtcca ataaatcgat cgttaattat    360
attacaaagt tttcgcattt                                               380

<210> SEQ ID NO 12
```

```
<211> LENGTH: 300
<212> TYPE: DNA
<213> ORGANISM: Oryza sativa

<400> SEQUENCE: 12
ggccaaggcg atctatgact gaattgccaa tgcaccagcc tgtctacatg atgaataaat      60
aaagagtcca tccagtgtga tggctcatgc ctgtgtgagt gtgactgaat ccatcagtgt     120
gtgtgtgtgt ttgtgtcaac catgtgtgaa tcaggtgtca aaaatcgtgg ctggaaatcc     180
atgtggtttc tagctttatg taaatgttgt ttgtgaaata taaatattgt tttgtgtatg     240
tgaattttac tctctcattt ttctcttgca ctcaccattc tattatagta atttttttaa     300

<210> SEQ ID NO 13
<211> LENGTH: 213
<212> TYPE: DNA
<213> ORGANISM: Oryza sativa

<400> SEQUENCE: 13
ctaggctact gtagctagct gtgcatgtat gtggtgtggt tactaaaata attagtgttt      60
tccttttgtt tggaagcata tgtgtggtga ataaatgatg aactccgatg ttcctctcta     120
taaatcttga tgattcgcta gctatccgta cgtcgttgtt ctttgatttg atgatgagat     180
tgaaaaatgg aatgtcatgc taaggagggt gcc                                  213

<210> SEQ ID NO 14
<211> LENGTH: 1812
<212> TYPE: DNA
<213> ORGANISM: Artificial sequence
<220> FEATURE:
<223> OTHER INFORMATION: Codon redesigned coding sequence

<400> SEQUENCE: 14
atggtccgtc ctgtagaaac cccaacccgt gaaatcaaaa aactcgacgg cctgtgggca      60
ttcagtctgg atcgcgaaaa actgtggaatt gatcagcgtt ggtgggaaag cgcgttacaa    120
gaaagccggg caattgctgt gccaggcagt tttaacgatc agttcgccga tgcagatatt     180
cgtaattatg cgggcaacgt ctggtatcag cgcgaagtct ttataccgaa aggttgggca    240
ggccagcgta tcgtgctgcg tttcgatgcg gtcactcatt acggcaaagt gtgggtcaat    300
aatcaggaag tgatggagca tcagggcggc tatacgccat tgaagccga tgtcacgccg     360 tatgttattg ccgggaaaag tgtacgtatc accgtttgtg tgaacaacga actgaactgg    420
cagactatcc cgccgggaat ggtgattacc gacgaaaacg gcaagaaaaa gcagtcttac    480
ttccatgatt tctttaacta tgccggaatc catcgcagcg taatgctcta caccacgccg    540
aacacctggg tggacgatat caccgtggtg acgcatgtcg cgcaagactg taaccacgcg    600
tctgttgact ggcaggtggt ggccaatggt gatgtcagcg ttgaactgcg tgatgcggat    660
caacaggtgg ttgcaactgg acaaggcact agcgggactt gcaagtggt gaatccgcac     720 ctctggcaac cggtgaagg ttatctctat gaactgtgcg tcacagccaa aagccagaca     780
gagtgtgata tctacccgct tcgcgtcggc atccggtcag tggcagtgaa gggcgaacag    840
ttcctgatta ccacaaaacc gttctacttt actggctttg gtcgtcatga agatgcggac    900
ttgcgtggca aaggattcga taacgtgctg atggtgcacg accacgcatt aatggactgg    960
attgggccaa ctcctaccg tacctcgcat taccttacg ctgaagagat gctcgactgg    1020
gcagatgaac atggcatcgt ggtgattgat gaaactgctg ctgtcggctt taacctctct    1080
ttaggcattg gtttcgaagc gggcaacaag ccgaaagaac tgtacagcga agaggcagtc    1140
```

| | |
|---|---|
| aacggggaaa ctcagcaagc gcacttacag gcgattaaag agctgatagc gcgtgacaaa | 1200 |
| aaccaccccaa gcgtggtgat gtggagtatt gccaacgaac cggatacccg tccgcaaggt | 1260 |
| gcacgggaat atttcgcgcc actggcggaa gcaacgcgta aactcgaccc gacgcgtccg | 1320 |
| atcacctgcg tcaatgtaat gttctgcgac gctcacaccg ataccatcag cgatctcttt | 1380 |
| gatgtgctgt gcctgaaccg ttattacgga tggtatgtcc aaagcggcga tttggaaacg | 1440 |
| gcagagaagg tactggaaaa agaacttctg gcctggcagg agaaactgca tcagccgatt | 1500 |
| atcatcaccg aatacggcgt ggatacgtta gccgggctgc actcaatgta caccgacatg | 1560 |
| tggagtgaag agtatcagtg tgcatggctg gatatgtatc accgcgtctt tgatcgcgtc | 1620 |
| agcgccgtcg tcggtgaaca ggtatggaat tcgccgatt ttgcgacctc gcaaggcata | 1680 |
| ttgcgcgttg gcgtaacaa gaaagggatc ttcactcgcg accgcaaacc gaagtcggcg | 1740 |
| gcttttctgc tgcaaaaacg ctggactggc atgaacttcg gtgaaaaacc gcagcaggga | 1800 |
| ggcaaacaat ga | 1812 |

```
<210> SEQ ID NO 15
<211> LENGTH: 324
<212> TYPE: DNA
<213> ORGANISM: Cauliflower mosaic virus

<400> SEQUENCE: 15
```

| | |
|---|---|
| ccgatcctac ctgtcacttc atcaaaagga cagtagaaaa ggaaggtggc acctacaaat | 60 |
| gccatcattg cgataaagga aaggctatca ttcaagatgc ctctgccgac agtggtccca | 120 |
| aagatggacc cccacccacg aggagcatcg tggaaaaaga agacgttcca accacgtctt | 180 |
| caaagcaagt ggattgatgt gatacttcca ctgacgtaag ggatgacgca caatcccact | 240 |
| atccttcgca agaccttcc tctatataag gaagttcatt tcatttggag aggacacgct | 300 |
| gaaatcacca gtctctctct acaa | 324 |

```
<210> SEQ ID NO 16
<211> LENGTH: 1399
<212> TYPE: DNA
<213> ORGANISM: Oryza sativa

<400> SEQUENCE: 16
```

| | |
|---|---|
| tcgaggtcat tcatatgctt gagaagagag tcgggatagt ccaaaataaa acaaaggtaa | 60 |
| gattacctgg tcaaaagtga aaacatcagt taaaggtgg tataaagtaa aatatcggta | 120 |
| ataaaggtg gcccaaagtg aaatttactc ttttctacta ttataaaaat tgaggatgtt | 180 |
| tttgtcggta ctttgatacg tcattttttgt atgaattggt ttttaagttt attcgctttt | 240 |
| ggaaatgcat atctgtattt gagtcgggtt taagttcgt ttgcttttgt aaatacagag | 300 |
| ggatttgtat aagaaatatc tttagaaaaa cccatatgct aatttgacat aatttttgag | 360 |
| aaaaatatat attcaggcga attctcacaa tgaacaataa taagattaaa atagcttcc | 420 |
| cccgttgcag cgcatgggta ttttttctag taaaaataaa agataaactt agactcaaaa | 480 |
| catttacaaa aacaacccct aaagttccta agcccaaag tgctatccac gatccatagc | 540 |
| aagcccagcc caacccaacc caacccaacc caccccagtc cagccaactg gacaatagtc | 600 |
| tccacaccc cccactatca ccgtgagttg tccgcacgca ccgcacgtct cgcagccaaa | 660 |
| aaaaaaaga aagaaaaaaa agaaaaagaa aaaacagcag gtgggtccgg gtcgtggggg | 720 |
| ccggaaacgc gaggaggatc gcgagccagc gacgaggccg gccctccctc cgcttccaaa | 780 |

```
gaaacgcccc ccatcgccac tatatacata cccccccctc tcctcccatc ccccaaccc    840 taccaccacc accaccacca cctccacctc ctcccccctc gctgccggac gacgagctcc   900
tcccccctcc ccctccgccg ccgccgcgcc ggtaaccacc ccgcccctct cctctttctt   960
tctccgtttt tttttccgtc tcggtctcga tctttggcct tggtagtttg ggtgggcgag  1020
aggcggcttc gtgcgcgccc agatcggtgc gcgggagggg cgggatctcg cggctggggc  1080
tctcgccggc gtggatccgg cccggatctc gcggggaatg gggctctcgg atgtagatct  1140
gcgatccgcc gttgttgggg gagatgatgg ggggtttaaa atttccgccg tgctaaacaa  1200
gatcaggaag aggggaaaag ggcactatgg tttatatttt tatatatttc tgctgcttcg  1260
tcaggcttag atgtgctaga tctttctttc ttcttttttgt gggtagaatt tgaatccctc  1320
agcattgttc atcggtagtt tttcttttca tgatttgtga caaatgcagc ctcgtgcgga  1380
gcttttttgt aggtagaag                                                1399
```